United States Patent [19]

Murdock

[11] 3,991,623
[45] Nov. 16, 1976

[54] MARINE INSTRUMENT

[75] Inventor: Lawrence C. Murdock, Bellevue, Wash.

[73] Assignee: Westinghouse Electric Corporation, Pittsburgh, Pa.

[22] Filed: Oct. 9, 1973

[21] Appl. No.: 404,565

[52] U.S. Cl............................................ 73/170 A
[51] Int. Cl.².................................... G01W 1/00
[58] Field of Search.................... 73/170 A, 170 R; 324/65 R

[56] References Cited
UNITED STATES PATENTS

| | | | |
|---|---|---|---|
| 2,616,950 | 11/1952 | Terpstra | 324/65 R |
| 3,221,556 | 12/1965 | Campbell et al. | 73/170 A |
| 3,278,844 | 10/1966 | Bell et al. | 324/65 R |
| 3,358,223 | 12/1967 | Birnstingl | 324/65 R |
| 3,470,465 | 9/1969 | Wuschke | 324/65 R |
| 3,604,258 | 9/1971 | Maiershofer | 73/170 A |

*Primary Examiner*—Richard C. Queisser
*Assistant Examiner*—Anthony V. Ciarlante
*Attorney, Agent, or Firm*—D. Schron

[57] ABSTRACT

An expendable instrument for determining salinity versus depth in a water column and suitable for use from vessels underway, from helicopters, and from fixed platforms. The salinity indication is obtained by the use of a conductivity cell for measuring the water conductivity, and a standard cell for measuring the conductivity of a standard sample, and obtaining the conductivity ratio. The resultant is transmitted up a wire link to processing equipment.

10 Claims, 11 Drawing Figures

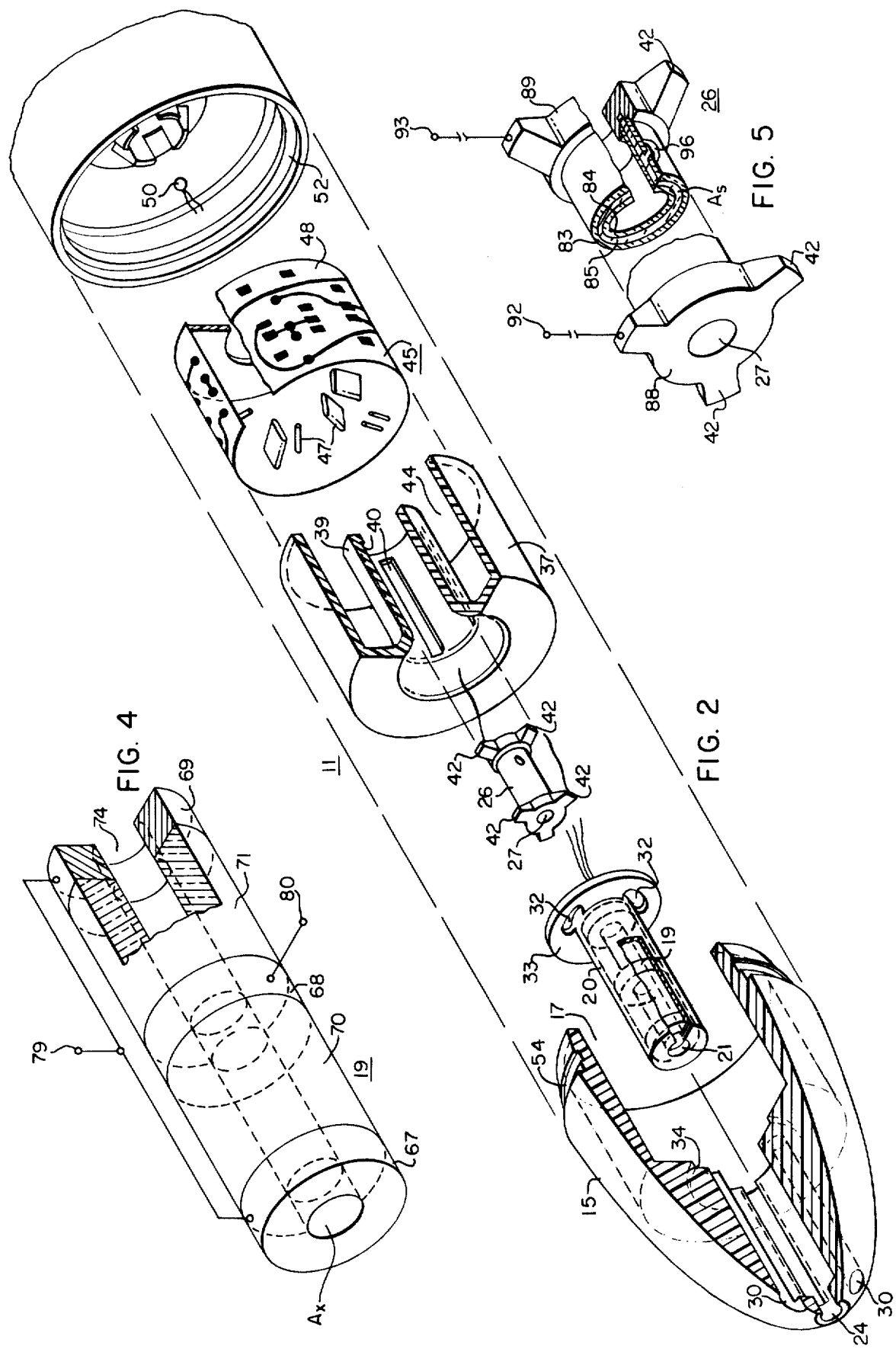

MARINE INSTRUMENT

BACKGROUND OF THE INVENTION

1. Field of the Invention

The invention in general relates to marine instruments, and particularly to an oceanographic probe which may be expendable.

2. Description of the Prior Art:

Both military and scientific vessels at sea routinely make measurements of the temperature distribution in the water column beneath the vessel using an instrument called a bathythermograph. The data from these measurements are used to determine the profile of the thermocline, that is, the boundary between the upper mixed water layer and the lower colder water. A knowledge of this thermocline profile adds to the knowledge of ocean circulation, is useful in fishery operations and can be used in the prediction of sonar propagation.

It is often impractical to stop or slow down the vessel to take the measurements due to the tactical situation in a military mission or the economics of ship operation. In order to overcome this limitation a probe has been developed which can be launched over a side of the vessel in motion and which contains a spool of wire which is paid out at a predetermined constant rate. A second spool of wire on board the vessel is paid out as the vessel moves. Such an arrangement is described in U.S. Pat. No. 3,221,556.

Although predictions can be made from the thermocline profile, a much more accurate assessment of sonar propagation, ocean circulation and fishery migration can be obtained with a knowledge of the water salinity.

Basically, salinity is a measure of the salt content of the water, typically seawater, and is a complex function of the temperature, conductivity and pressure of the seawater sample. Salinity can be determined by adding a conductivity cell to the probe and measuring the independent variables of temperature and conductivity and combining them with an indication of pressure, by means of an analog or digital computer. In order to achieve a salinity accuracy of 0.1 parts per thousand it is necessary to measure temperature to 0.05° C and conductivity to 0.05 millimhos, which requires a measuring system accurate to 0.1%. It would be desirable to have an instrument operable in the rigors of an at sea environment for long periods of time which would achieve the desired accuracy for salinity with the use of components having a less stringent accuracy requirement.

In addition, conductivity measurements have inherently nearly instantaneous response whereas temperature measurements inherently have a lag associated with their basic sensing device such as a thermistor. Accordingly the method of utilizing the temperature and conductivity readings to compute salinity cannot be utilized with accuracy in waters having high thermal gradiants.

The present invention allows for an oceanographic probe which provides an indication of salinity to a very high degree of accuracy and which can be used to obtain salinity measurements in the presence of high thermal gradients of the water column.

SUMMARY OF THE INVENTION

The marine instrument of the present invention includes a body which can be placed in a water environment, towed through the water or dropped through a water column and includes two conductivity cells. A first cell is an in situ conductivity cell for measuring the conductivity of the water environment acting on the cell and a second cell is a standard cell for measuring the conductivity of a standard sample of water of a known salinity and which conductivitychanges with different temperatures. The coductivity changes are arranged within the body and in an electric circuit so as to obtain an output signal which is proportional to the ratio of the two conducivity cell measurements at substantially the same temperature. This output signal which is proportional to the conductivity ratio is also an indication of salinity since by international agreement salinity is defined in terms of this conductivity ratio, and means are provided for conveying this output signal to a utilization device by which salinity can then be determined.

Where salinity determination is made at a remote location the conductivity measurements may be sent via a wire link to computation equipment either as separate measurements or as the conductivity ratio measurement previously mentioned.

BRIEF DESCRIPTION OF THE DRAWINGS

FIG. 2 is an exploded view, with portions broken away, of the nose section of the probe of FIG. 1;

FIG. 4 is a view with a portion broken away of a conductivity cell of the probe;

FIG. 5 is a view with a portion broken away, of another conductivity cell of the probe;

DESCRIPTION OF THE PREFERRED EMBODIMENT

Figure 1:
FIG. 1 is a view of an oceanographic probe.

The marine instrument illustrated in FIG. 1 is in a form of an oceanographic probe 10 having a nose section 11 and a tail section 12 defining a hydrodynamic body which is dropped through the water column. Due to the hydrodynamic shape and ballast or weighting considerations, the probe 10 will drop through the water column, nose section first, at a constant drop rate.

The exploded view, with portions broken away, of FIG. 2 illustrates the nose section 11 in more detail. The nose section includes a body portion 15 having a large cavity 17 for the placement of certain components. Ballast weights may be molded into the body portion 15, or the body portion 15 itself may be considered as the ballast and may be molded from various materials such as plastics or metals. A first cell 19 is provided for obtaining the conductivity of the water environment acting on the cell and in this respect it is considered as an in situ conductivity cell. The in situ cell 19, which will be described with respect to FIG. 4, is placed in an electrically insulating container or envelope 20 having a hole 21 at the end thereof and the unit is placed into a primary or central flow path 24 whereby as the probe drops through the water column, the water whose conductivity is to be measured passed through the central flow path and in so doing passes through the hole 21 in the container 20 and through the central portion of the in situ cell 19.

In addition to the first cell, there is included a second conductivity cell in the form of a standard cell described with respect to FIG. 5, and which provides an indication of the conductivity of a standard sample of seawater contained therein. The standard cell 26 is in close proximity to the in situ cell 19 so that both conductivity measurements are made at substantially the same water temperature.

The standard cell 26 has an axial passage 27 therethrough which lines up with the axial passage of the in situ cell 19 and in order to increase the water flow through and around the standard cell there is provided a plurality of auxiliary flow paths 30 whereby water flows past the in situ cell 19 but does not contact it due to the container 20 and then passes through a plurality of apertures 32 in the disc-like end section 33 of the container and which end section 33 fits into a mating recess 34 when assembled in the body portion.

Means are provided for supporting the standard cell 26, and preferably for supporting it in line with the primary flow path 24. One way of accomplishing this is by the provision of a housing 37 having a central cylindrical portion 39 with a plurality of longitudinal slots 40 for receiving tabs or projections 42 on the standard cell 26 in order to hold it in position. When so positioned, water entering the nose section through the primary and auxiliary flow paths passes axially through and around the standard cell 26.

The support for the standard cell is conveniently shown as being incorporated into a removable housing, however, it is possible for the support to be molded as a part of the body portion 15.

Around the central cylindrical portion 39 there is defined an annular cavity 44 for reception of the electronics section 45 which has a plurality of electric circuit components 47 mounted on a printed circuit board 48 of a size and shape to conveniently slip into the annular cavity 44. Many variations for this configuration exist, including the pre-potting of the electronic components into cylindrical form for insertion around the central cylindrical portion 39 or the insertion of the electronic components and the subsequent potting thereof.

The arrangement herein eliminates the need for obtaining salinity indications by using a temperature measurement. However, it is often desirable to have an indication of the temperature profile as the probe drops through the water column and accordingly a temperature measuring device such as thermistor 50 may be included and positioned in the nose section so that the ambient water medium acts upon it.

A portion of the tail section 12 is illustrated and the interior thereof includes a plurality of lands and grooves 52 for complementary engagement with lands and grooves 54 of the body portion 15 to form a press fit locking arrangement.

Figure 3:
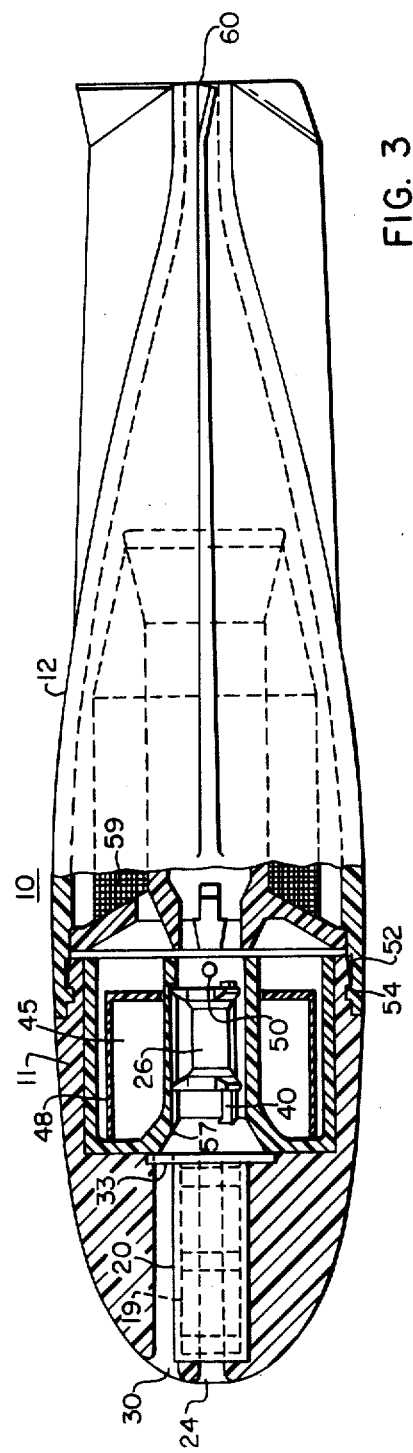
FIG. 3 is a cross section through the probe of FIG. 1.

FIG. 3 illustrates the components of FIG. 2 in nested relationship for dropping through the water column. In the partial cross sectional view only one auxiliary flow path 30 is illustrated and it is seen that this path terminates adjacent the mouth of the housing 39 having sloping sidewall portions 57 for directing the incoming water to the standard cell 26 for location.

The tail section 12 includes a spool of wire arrangement 59 which pays out through an opening 60 in the end of the tail section 12 such arrangements being well known to those skilled in the art and described for example in U.S. Pat. No. 3,221,556.

FIG. 4 is a more detailed view, with a portion broken away, of the in situ cell 19. The in situ cell 19 includes a plurality of electrodes 67, 68, and 69 separated by insulating spacer members 70 and 71. In situ seawater flows through the hollow middle 74 of the cell and the cell is continually flushed as the probe is dropped, thereby bringing fresh fluid at the new depth into contact with the electrodes. In order to prevent any shunt conductance path between electrodes as in a two electrode cell which would result in a measurement error, the in situ cell has three electrodes with the two end electrodes 67 and 69 electrically connected together and connected to terminal 79, while the middle electrode 68 is connected to terminal 80.

The resistance $R_x$ between the terminal 79 and 80 is:

$$R_x = \frac{1}{\sigma_x} \frac{L_x}{A_x} \quad (1)$$

where $L_x$ is the length between the middle of the electrodes 67 and 68 (or 68 and 69, the distances being equal), $A_x$ is the cross sectional area of the hollow middle in which the water flows, and $\sigma_x$ is the conductivity of the water in the cell.

Since $L_x$ and $A_x$ are fixed, their ratio is fixed and Equation (1) reduces to $$R_x = \frac{1}{\sigma_x} K_x$$

where $K_x$ is the cell constant equal to $L_x/A_x$.

During operation, water continually fills the interior 74 of the in situ cell 19 and it is desired to eliminate or minimize any water contact with the outside of the cell which would cause undesirable variations. For this purpose there is provided the container 20 illustrated in FIG. 2. As an alternative, electrodes such as 67, 68, and 69 may be molded directly into the body portion of the nose section, if it is of an insulating material, with an axial passage through the electrodes for water.

The success of measuring the conductivity ratio depends upon transporting a sample of standard seawater along with the probe and keeping the temperature of the standard seawater at substantially the same temperature as the ambient water. The standard cell 26 illustrated with a portion broken away, in FIG. 5 can accomplish this function. The standard cell includes two concentric thin wall cylinders 83 and 84 separated by a thin film 85 of standard seawater of known salinity, for example 35 parts per thousand. The cylinders 83 and 84 are of a material having a high thermal and low electrical conductivity along with good mechanical properties, high purity alumina being an example.

Electrodes 88 and 89 are located on either end of the cell and make electrical contact with the cylindrical thin film of water 85 and are connected to respective terminals 92 and 93. The resistance $R_s$ measured at terminals 92 and 93 is:

$$R_s = \frac{1}{\sigma_s} \frac{L_s}{A_s} \qquad (3)$$

where $L_s$ is the length of the thin film cylinder of standard seawater, $A_s$ is the area of the thin film of standard seawater and $\sigma_s$ is the conductivity of the standard seawater.

The cell constant $K_s$ is defined by the term $L_s/A_s$ and Equation (3) reduces to $$R_s = \frac{1}{\sigma_s} K_s \qquad (4)$$

A flexible seal 96 is utilized in order to pressure compensate the standard water filled interior between the cylinders 83 and 84.

Due to the cell construction it has an extremely rapid time constant to quickly bring the thin film of water to the temperature of the surrounding ambient water so that a conductivity ratio can be obtained from conductivities measured at substantially the same temperaure as required by international agreement. It is to be noted that the salinity of the thin film water sample remains constant, however, its conductivity is subject to change with different temperatures and may vary for example, within a certain temperature range, of from 0.0275 mhos/cm to 0.063 mhos/cm. Due to the fact that both cells are at substantially the same temperature however their ratio would vary from approximately 0.8710 at a salinity of 30 parts per thousand to 1.1261 at a salinity of 40 parts per thousand.

Figure 6:
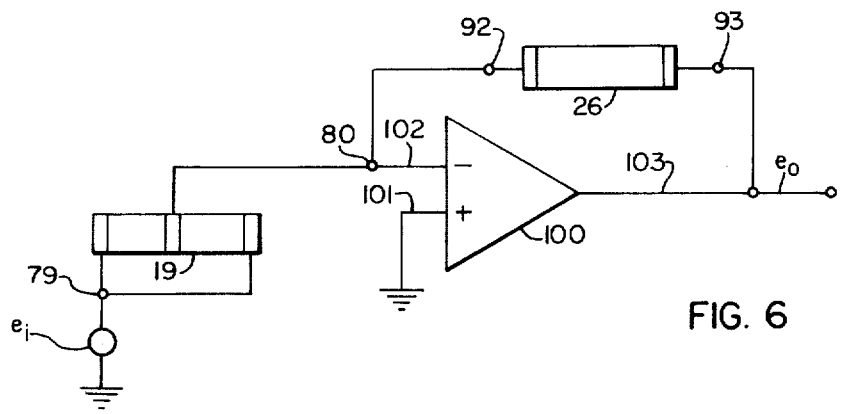
FIG. 6 is an electric circuit utilizing the conductivity cells of FIGS. 4 and 5.

The two cells are connected in an electric circuit operable to provide an output signal proportional to the ratio of the conductivity of the water environment acting on the in situ cell with respect to the conductivity of the standard cell. Such a circuit is illustrated in FIG. 6.

A high gain operational amplifier 100 has a non-inverting, or positive input 101, an inverting or negative input 102, and an output 103. The in situ cell 19 is connected between an ac source $e_i$ and the negative input 102, and the standard cell 26 is connected in a feedback relationship between the output 103 and the negative input 102. The positive input 101 is connected to a reference potential such as ground.

The ratio of the output voltage $e_o$ to the input $e_i$ is given by:

$$\frac{e_o}{e_i} = \frac{R_s}{R_x} \frac{A}{(1-A)} \qquad (5)$$

where $R_s$ is the resistance of the standard cell 26, $R_x$ is the resistance of the in situ cell 19, and $A$ is the open loop gain of the amplifier 100. Since the amplifier 100 is a high gain amplifier (e.g. 10,000) Equation (5) reduces to:

$$\frac{e_o}{e_i} = - \frac{R_s}{R_x} \qquad (6)$$

substituting from Equation (1) and (2):

$$\frac{e_o}{e_i} = - \frac{\frac{1}{\sigma_s} \frac{L_s}{A_s}}{\frac{1}{\sigma_x} \frac{L_x}{A_x}} \qquad (7)$$

substituting the cell constants:

$$\frac{e_o}{e_i} = - \frac{\sigma_x K_s}{\sigma_s K_x} \qquad (8)$$

since the cell constants do not change, $K_s/K_s$ may be replaced by another constant K so that:

$$e_o = e_i K \frac{\sigma_x}{\sigma_s} \qquad (9)$$

Equation (9) shows that the output signal from the circuit of FIG. 6 is proportional to the ratio of the conductivities and is, by definition, therefore proportional to the salinity of the water sample being measured due to the fact that the arrangement of the components of the probe are such that the measurements are being made at substantially the same temperature. The standard cell 26 is shown in the feedback path between the output and the input of the amplifier 100, however the in situ cell and standard cell positions can be reversed, for which case the output signal would be proportional to the conductivity ratio $\sigma_s/\sigma_x$.

A signal is thus obtained which is indicative of salinity and accordingly means are provided for conveying such signal to some sort of a utilization means. If the probe is designed to be retrievable and is of sophisticated construction, such utilization means may be an on board recorder. Where the probe is dropped through the water column the output signal indicative of the conductivity must be related to depth. Such recorder could also register depth information from an on board depth recorder.

Where salinity must be known concurrently with the dropping of the probe, the utilization means would be at a remote location, such as on board the vessel dropping the probe and the means for conveying the output signal indicative of conductivity ratio would include the output 103 from amplifier and at least the wire 59 (FIG. 3) which in that instance would be adapted as a wire link for conveying electrical signals.

If there is a requirement to additionally know one or more of the individual conductivity measurements, they may be separately recorded or transmitted to the remote location where they then may be combined as in FIG. 6. To just transmit the output signal up the wire link however risks accuracy due to the possibly severe attenuation of the signal over the long distance from the probe to the utilization device and accordingly it is preferable that some sort of conversion means be provided to minimize loss of accuracy. For example the conversion device could be a voltage controlled oscillator, the frequency of which is governed by the output signal indicative of salinity. However, this method is not known for low cost, long term stability, nor freedom from variation due to power supply variation or ambient temperature change, all of which are necessary if the instrument is to be expendable. A preferred arrangement for conveying the output signal to a remote location is as illustrated in FIG. 7.

Figure 7:
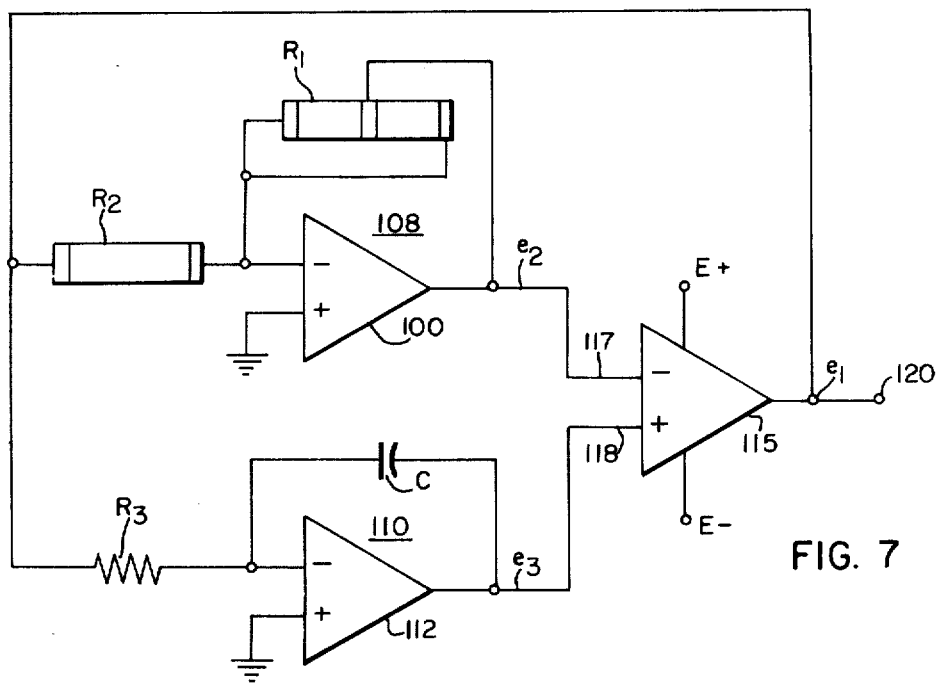
FIG. 7 is an electric circuit for converting conductivity ratio to an oscillator output.

In FIG. 7 there is included a first circuit means 108 for providing a first output signal indicative of a desired measured parameter, in the present example, conductivity ratio. The first circuit means 108 is similar to that described in FIG. 6, however, the positions of the conductivity cells have been reversed. The in situ conductivity cell is designated $R_1$ and is in the feedback of amplifier 100 while the standard cell, designated $R_2$ is in the input path.

A second circuit means 110 is operable to provide a second signal which varies linearly with time and includes an amplifier 112 similar to amplifier 100 and having in its feedback path a capacitor C, and a resistance $R_3$ in its input.

An output amplifier 115 includes first and second inputs 117 and 118, 117 being the negative or inverting input and 118 being the positive or non-inverting input. The power supply connections for the amplifier 115 are illustrated as being for connection to a positive power source designated $E^+$ and to a negative power source $E^-$. The output of amplifier 115 in addition to being supplied to an output terminal 120 is also fed back to serve as the input signal to the first and second circuits 108 and 110.

The operation of the first circuit 108 has been described and its output $e_2$ is a voltage proportional to the conductivity ratio derived from the two conductivity cells in its input and feedback arms.

With respect to the second circuit 110, it is to be noted that an operational amplifier such as amplifier 112, with a feedback works in a direction to make its two inputs equal. Assuming a square wave input to resistor $R_3$ and of magnitude E then:

$$E = i R_3 \tag{10}$$

where $i$ is the current through both $R_3$ and C. The output $e_3$ of amplifier 112 due to the nature of the amplifier is:

$$e_3 = \frac{1}{C} \int i \, dt \tag{11}$$

Since $e$ is a square wave input its magnitude would be a constant positive or negative value and therefore the current $i$ would be constant so that:

$$e_3 = \frac{i}{C} t \tag{12}$$

Therefore Equation (12) shows that the output $e_3$ varies linearly with time and due to the nature and operation of the amplifier 112, $e_3$ will go negative when E is positive, and vice versa. The amplifiers described herein are commercially available items well known to those skilled in the art.

Output $e_1$ of amplifier 115 will switch between saturation values $E^+$ and $E^-$ whenever the inputs to amplifier 115 are equal, or substantially equal. In a typical commercially available operational amplifier such switching will occur when the difference is fractions of a millivolt, which is the differential input voltage that produces saturation. Accordingly the output $e_i$ can be considered as a square wave which switches between values $E^+$ and $E^-$ and this square wave is fed back to the first and second circuits 108 and 110.

Figure 7A:
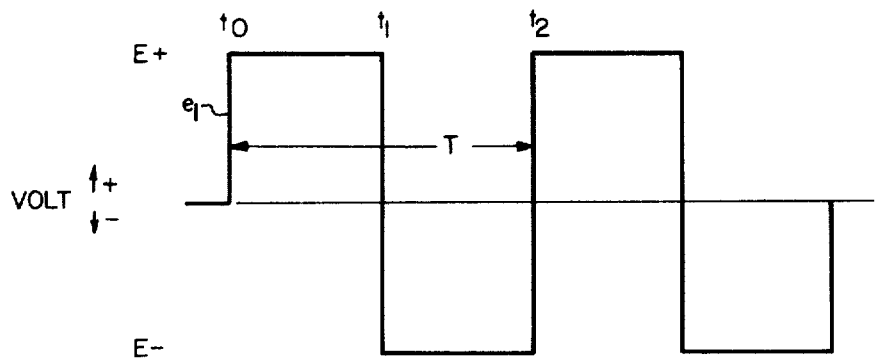
FIGS. 7A and 7B are waveforms illustrating the operation of the circuit of FIG. 7.
Figure 7B:
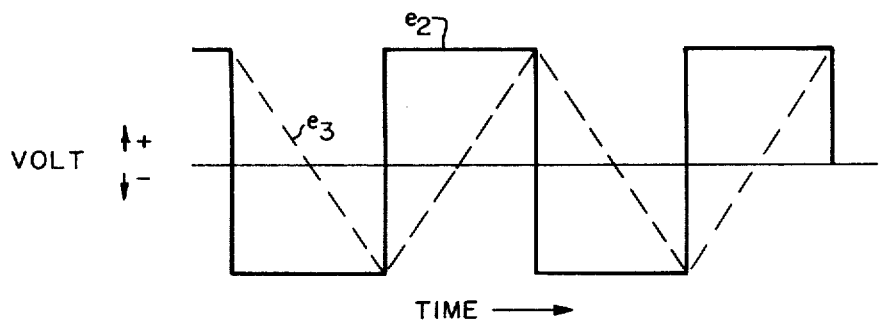

FIG. 7A illustrates the output signal $e_i$ having the saturation value $E^+$ from time $t_0$ to $t_1$ and having the negative saturation value $E^-$ from $t_1$ to $t_2$, the time from $t_0$ to $t_2$ constituting the period T. Since this waveform is applied to the inverting input of amplifier 100, the output $e_2$ will be an opposite version of the input and this waveform is illustraed in FIG. 7B.

The square wave $e_i$ is also applied as the input to the second circuit 110 which, it will be remembered, provides an output signal $e_3$ which linearly varies with time the linear rate being determined by $R_3C$ and has a slope which is opposite in polarity to the input. $e_3$ is shown as the dotted line waveform of FIG. 7B and it is seen, for example, that from time $t_0$ to $t_1$ the voltage of $e_3$ approaches that of $e_2$, and at time $t_1$ they are equal in magnitude thus causing a switch to the opposite state of amplifier 115 as can be seen by the waveform of FIG. 7A. The negative voltage fed back thus causes $e_2$ to reverse polarity and $e_3$ to reverse direction until $t_2$ at which time $e_2$ and $e_3$ are equal to again cause switching of amplifier 115.

It may be shown that for equal positive and negative supply voltages E, the circuit will oscillate with a period T of:

$$T = 4 R_3 C \frac{R_1}{R_2} \tag{13}$$

It will be remembered that the quantity $R_1/R_2$ is proportional to the conductivity ratio of the standard to the in situ conductivity cells and since $R_3$ and C are constant, the period T is directly proportional to this conductivity ratio and independent of power supply voltage as long as the positive and negative power supply voltages are equal. However a variation of 6% in the power supply voltage ratio would result in less than 0.1% variations in the output frequency or period.

$$(\text{Period} = \frac{1}{\text{frequency}})$$

By way of example, for a center frequency of 1.150 kilohertz (Khz), values of $R_3$ and C could be 2.2 K ohms and 0.1 microfarad respectively. The in situ cell $R_1$ could be designed to vary from between 89 to 278 ohms and the standard cell from 890 to 2780 ohms depending upon the water conductivity and the temperature. With these values FIG. 7C illustrates a plot of output frequency versus conductivity ratio.

Figure 8:
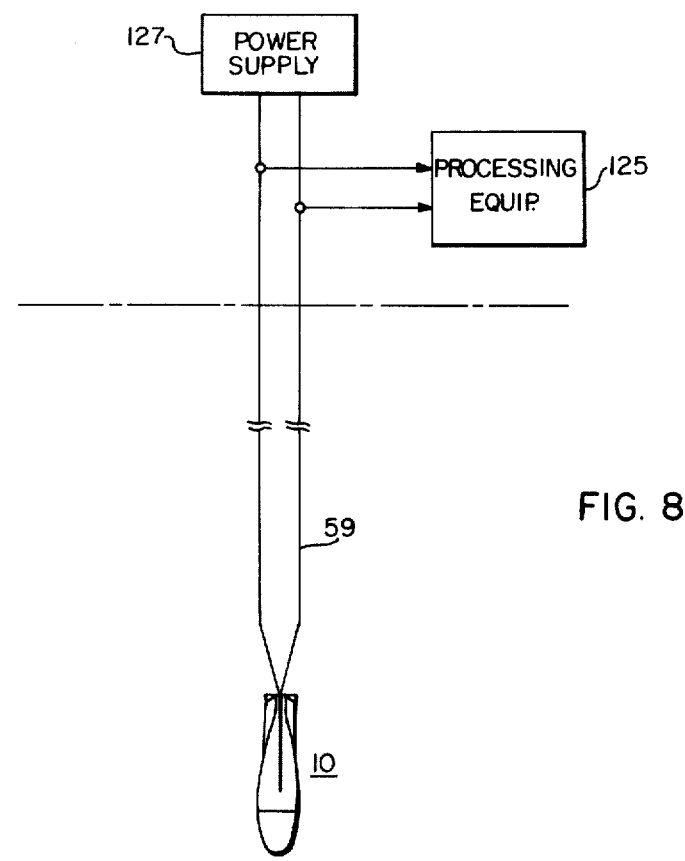
FIG. 8 illustrates the signal and power communication between the probe in the ocean and a remote location.
Figure 7C:
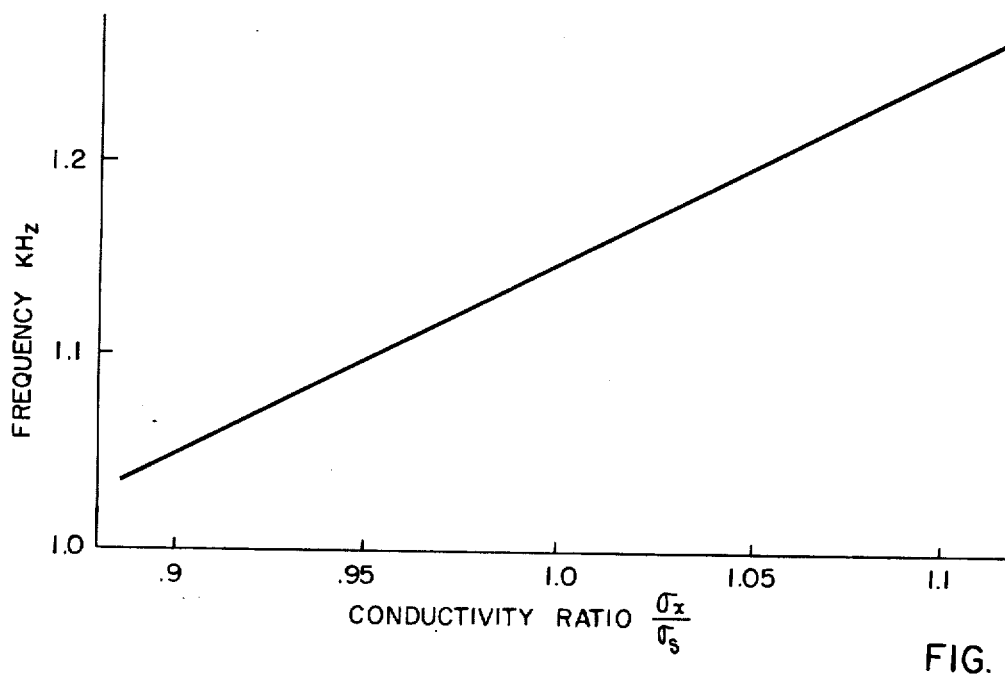
FIG. 7C is a graph illustrating frequency vs. conductivity ratio for the circuit of FIG. 7.

The output signal $e_3$ therefore has a period (or frequency) which is directly proportional to conductivity ratio and this signal may be sent up the wire link 59, as illustrated in FIG. 8, to be fed to on board processing equipment 125 for interpreting the signal by measuring its period (or frequency) for determining conductivity ratio by hand with the use of a conversion chart such as in FIG. 7C, or automatically by use of a computer look-up table or by directly obtaining salinity from the output signal. The conductivity ratio at any point in the drop must be correlated with the distance from the surface. Again this can be accomplished by a depth device such as a pressure transducer transmitting a signal up the wire link 59 or can be surmised due to the fact that the sink rate is a constant and is known. The power supply 127 for the electronics is provided via the same wire link 59 that transmits the information from the probe to the on board equipment and is preberably a constant current dc source so that the effects of wire resistance can be neglected.

I claim as my invention:

1. A marine instrument comprising:
   a. a body for use in the water environment and having a nose portion which includes a primary flow path through said nose portion for passage of said water environment;

b. a first cell for measuring the conductivity of said water environment acting on said first cell, and having a central passage therethrough;
c. a standard cell for measuring the conductivity of a standard sample of water, and having a central passage therethrough;
d. said first and standard cells being carried by said body for performing measurements at substantially the same temperature;
e. said first and standard cells being positioned in said primary flow path;
f. said water environment in said primary flow path, passing through said central passages; and
g. circuit means for conveying an indication of said measurements to a utilization means.

2. Apparatus according to claim 1 wherein said circuit means includes:
a. an electric circuit including said first and standard cells and operable to provide an output signal proportional to the ratio of the conductivity of said water environment acting on said first cell, and the conductivity of said standard cell.

3. Apparatus according to claim 2 which includes:
a. a wire link for conveying an indication of said output signal to a remote location.

4. Apparatus according to claim 1 wherein:
a. said body is of a hydrodynamic shape for dropping through the water column.

5. Apparatus according to claim 1 wherein: said water environment in said primary flow path additionally passes around the outside of said standard cell.

6. Apparatus according to claim 1 wherein:
a. said first and standard cells are serially positioned within said nose portion.

7. Apparatus according to claim 1 which additionally includes:
a. at least one auxiliary flow path by passing said central passage of said first cell and communicating with said standard cell.

8. Apparatus according to claim 1 wherein:
a. said first cell includes a plurality of spaced annular electrodes;
b. insulating means separating said electrodes;
c. an electrically insulating container surrounding said cell and having openings for passage of said water environment through said annular electrodes.

9. Apparatus according to claim 1 which includes:
a. a compartment around said standard cell;
b. electronic circuitry located in said compartment for obtaining the ratio of the conductivity of said water environment acting on said first cell, and the conductivity of said standard cell.

10. Apparatus according to claim 1 which includes:
a. a housing including a central cylindrical portion;
b. the interior of said cylindrical portion including a plurality of longitudinal slots;
c. said standard cell including a plurality of projections for complementary engagement with said slots for holding said standard cell in position.

* * * * *